United States Patent [19]
Lutz

[11] Patent Number: 6,132,408
[45] Date of Patent: Oct. 17, 2000

[54] DRAINAGE SYSTEM FOR UROSTOMY BAG

[76] Inventor: Vivian M. Lutz, 3650 Berry Rd., P.O. Box 115, Pleasant Lake, Mich. 49272

[21] Appl. No.: 09/098,808

[22] Filed: Jun. 17, 1998

[51] Int. Cl.[7] ....................................................... A61F 5/44
[52] U.S. Cl. ............................................................. 604/335
[58] Field of Search .................................... 604/276–278, 604/905, 326, 332–345

[56] References Cited

U.S. PATENT DOCUMENTS

| | | | |
|---|---|---|---|
| 2,759,477 | 8/1956 | Mains | 128/295 |
| 2,800,905 | 7/1957 | Simmons et al. | |
| 2,883,985 | 4/1959 | Evans . | |
| 3,604,421 | 9/1971 | Pizzella . | |
| 3,823,716 | 7/1974 | Hale . | |
| 3,881,486 | 5/1975 | Fenton | 128/283 |
| 4,036,235 | 7/1977 | Hathaway | 128/292 |
| 4,326,521 | 4/1982 | Marsan | 128/283 |
| 4,417,892 | 11/1983 | Meisch | 604/323 |
| 4,449,971 | 5/1984 | Cawood | 604/328 |
| 4,460,362 | 7/1984 | Bates . | |
| 4,534,766 | 8/1985 | Steer et al. | 604/323 |
| 4,588,402 | 5/1986 | Igari et al. | 604/408 |
| 4,795,435 | 1/1989 | Steer . | |
| 5,087,251 | 2/1992 | Heyman et al. | 604/327 |
| 5,135,199 | 8/1992 | Cross et al. | 604/326 |
| 5,236,426 | 8/1993 | Schottes et al. . | |
| 5,267,989 | 12/1993 | Moyet-Orttiz | 604/349 |
| 5,919,146 | 7/1999 | Propp | 600/577 |

*Primary Examiner*—John G. Weiss
*Assistant Examiner*—Carie Mager
*Attorney, Agent, or Firm*—Mary M. Moyne; Ian C. McLeod

[57] ABSTRACT

A drainage system (10) for use with a Urostomy bag (100) is described. The drainage system includes a drainage tube (12) having a connector (18) at one end (12A) and a clamp (14) at the opposite discharge end (12B). An attachment clip (16) is mounted on the tube between the ends. The tube is connected by the connector to the bottom opening (100B) of the bag. When the bag is in position on a user (150), the clip attaches the discharge end of the tube to the user's clothing where the end is easily accessible.

13 Claims, 3 Drawing Sheets

DRAINAGE SYSTEM FOR UROSTOMY BAG

BACKGROUND OF THE INVENTION

(1) Field of the Invention

The present invention relates to a drainage system for use with a Urostomy bag. In particular, the present invention relates to a flexible drainage tube which is connected to the bottom opening of a Urostomy bag. The tube has a valve at one end to prevent leakage of the tube and has a clip which allows a user to clip the end of the tube at a location on the clothing which allows easy access to the tube for drainage of the bag.

(2) Description of the Related Art

The related art has shown various types of containers for holding bodily fluids. The containers have a variety of types of drainage systems. Illustrative are U.S. Pat. No. 2,883,985 to Evans; U.S. Pat. No. 3,604,421 to Pizzella; U.S. Pat. No. 3,823,716 to Hale and U.S. Pat. No. 4,460,362 to Bates. Evans and Pizzella show the use of a hose connected to a valve at the bottom of a urine collection bag which allows for draining the bag. Hale and Bates show bags for retaining urine which have drainage valves at the bottom of the bag.

Also of interest are U.S. Pat. No. 4,795,435 to Steer and U.S. Pat. No. 5,236,426 to Schbttes et al which show devices for protecting a wound which have bags which can be drained.

Only of minimal interest is U.S. Pat. No. 2,800,905 to Simmons et al which shows a douche bag.

There remains the need for a drainage system for a Urostomy bag which allows a user to quickly and easily empty the bag in a standing position.

SUMMARY OF THE INVENTION

In the past, it has been difficult to quickly and non-conspicuously drain a Urostomy bag. To drain the bag, a user would need to position the bottom opening of the bag directly over the waste receptacle. Due to the positioning of the bag and the positioning of standard waste receptacles (toilets), a user was required to remove or rearrange their clothing to expose the bottom opening of the bag. Next, the user would need to move the bottom of the bag away from the clothing to avoid soiling the clothing. Finally, the user would kneel next to the waste receptacle so that the bottom opening of the bag was directly and only slightly above the opening of the waste receptacle. The above process is extremely difficult and unappealing, particularly in a public restroom. The limited size of the restroom stalls hinders a user's ability to position the bottom opening of the bag directly over the waste receptacle. Further, the unsanitary conditions of many public rest areas makes users unwilling to kneel adjacent the waste receptacle as necessary to assure that the bag is emptied without escape of waste fluid.

The present invention allows a user to quickly and easily drain the bag into a standard waste receptacle from a standing position. The present invention provides a drainage system having a tube with a clip adjacent the discharge end which allows the user to clip the discharge end of the tube in a readily accessible position. The tube also has a valve at the discharge end which allows the user easy and convenient access to the valve which drains the bag. Convenient and quick access to the discharge end and valve allows for easy emptying of the bag by a user.

The substance and advantage of the present invention will become increasingly apparent by reference to the following drawings and the description.

DETAILED DESCRIPTION OF THE PREFERRED EMBODIMENTS

The present invention relates to a drainage system for use with a Urostomy bag, which comprises: a tube having first and second ends and configured to be connected at the first end to a bottom opening of the Urostomy bag; a shut-off means mounted on the second end of the tube for opening and closing the second end of the tube; and an attachment means mounted on the tube between the ends of the tube to allow attachment of the tube to clothing of a user.

Further, the present invention relates to an improved Urostomy bag having a top opening for securing to a user and a bottom opening for draining the bag, the bottom opening having a valve means for opening and closing the bottom opening, the improvement which comprises: a drainage tube having opposed ends and connected at one of the ends on the bottom opening of the bag; a shut-off means mounted on the other end of the tube for opening and closing the other of the ends of the tube; and an attachment means mounted on the tube between the ends of the tube to allow attachment of the tube to a user's clothing.

Still further, the present invention relates to a method for draining waste fluid from a Urostomy bag secured to a user, which comprises the steps of: providing a drainage system connected to a bottom opening of the Urostomy bag which includes a tube having first and second ends and configured to be connected at the first end to the bottom opening of the Urostomy bag; a shut-off means mounted on the second end of the tube for opening and closing the second end of the tube; and an attachment means mounted on the tube between the ends of the tube to allow attachment of the tube to clothing of the user wherein the first end of the tube is connected to the bottom opening of the Urostomy bag and wherein the tube is attached to the user's clothing using the attachment means; unfastening the user's clothing to allow access to the attachment means; unattaching the attachment means and the tube from the clothing of the user; positioning the second end of the tube over a waste receptacle; and opening the shut-off means and allowing the waste fluid to be drained from the bag into the waste receptacle.

Figure 2:
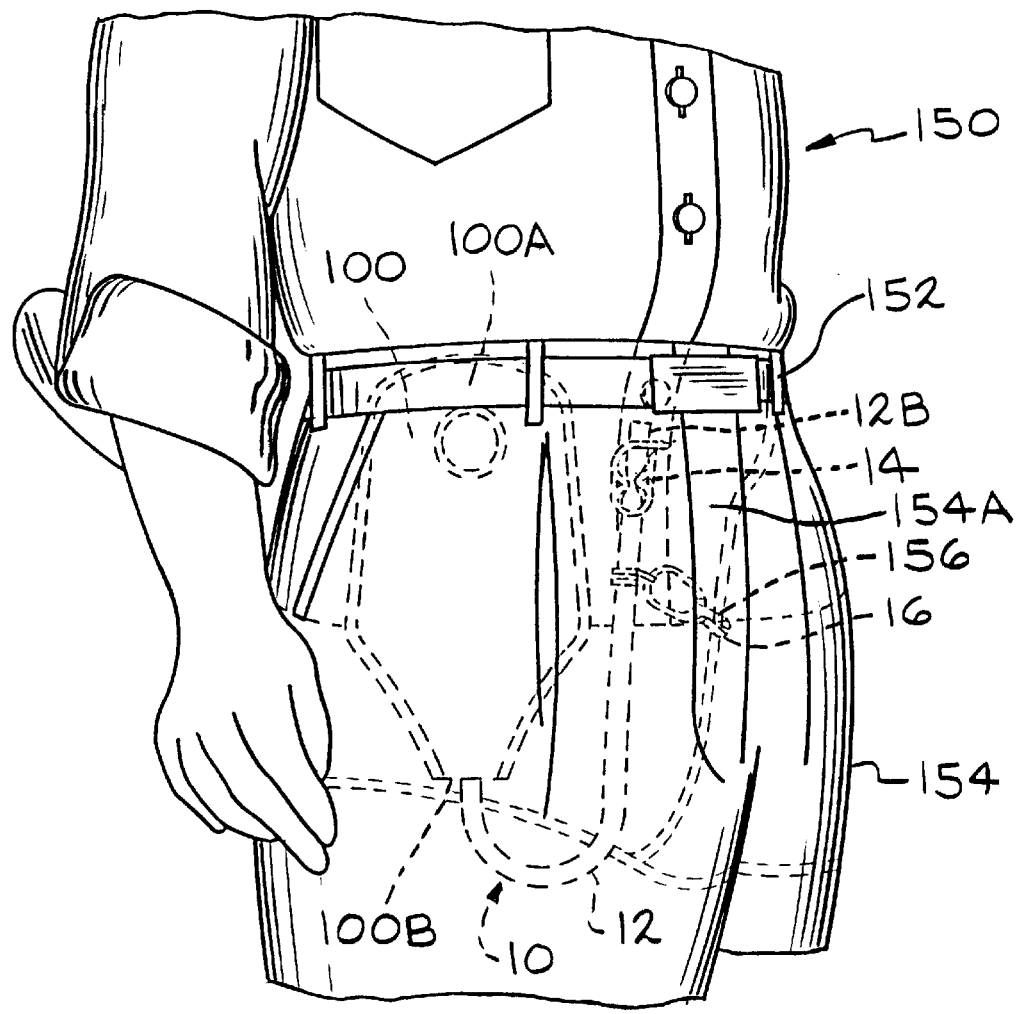
FIG. 2 is a perspective view of a user 150 having a Urostomy bag 100 with the tube 12 of the drainage system 10 clipped to the front opening 154A of the user's trousers 154.
Figure 3:
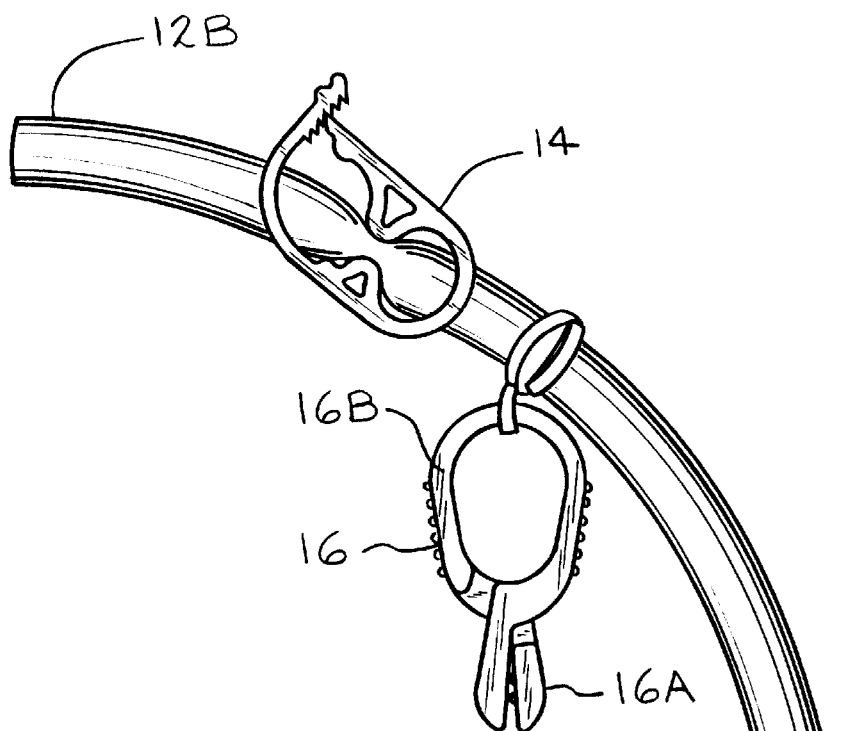
FIG. 3 is a front view of the drainage system 10 showing the tube 12, the clip 16 and the shut-off clamp 14.

FIG. 3 shows the drainage system 10 of the present invention. The system 10 is intended to be attached to the bottom opening 100B of a standard Urostomy bag 100. A standard Urostomy bag 100 has a top opening 100A which is mounted over the stoma opening (not shown) of the user 150. The bag 100 extends downward adjacent the waist 152 of the user 150. Preferably, the bag 100 is positioned offset to one side from the front and center of the user 150 (FIG. 2). It is understood that the bag's position is dependent on the location of the stoma of the user 150. The standard Urostomy bag 100 also has a bottom opening 100B at the bottom, center of the bag 100. The lower portion 100C of the bag 100 is funnel-shaped such as to direct the waste fluid or urine toward the bottom opening 100B. A standard Urostomy bag 100 is preferably similar to the standard Urostomy pouch sold under the trademark SUR-FIT® system by ConvaTec Limited located in Deeside, United Kingdom. A valve 102 can also be provided in the bottom opening 100B of the bag 100. The valve 102 allows the user 150 to sealingly close the bag 100. The standard Urostomy bag 100 with the valve 102 is preferably similar to the Urostomy pouch with ACCUSEAL® Tap sold under the trademark SUR-FIT® Natura™ by ConvaTec Limited located in Deeside, United Kingdom.

The drainage system 10 of the present invention includes a tube 12, a connector 18, a shut-off clamp or valve 14 and an attachment clip 16 mounted to the tube 12 (FIG. 3). The tube 12 has an inlet end 12A and a discharge end 12B. The tube 12 is flexible and preferably has a constant diameter along its length. The length of the tube 12 depends on the position of the bottom opening 100B of the bag 100 with respect to the front opening 154A of the user's trousers 154. The tube 12 should be of such a length that the discharge end 12B of the tube 12 can be easily positioned over the opening of a waste receptacle (not shown) such as a toilet or urinal. In the preferred embodiment, the tube 12 has a length of about 13 inches (33 cm). Preferably, the tube 12 is shorter when the user is female. The tube 12 is preferably made of a flexible material such as rubber or plastic which is impervious to urine.

The inlet end 12A of the tube 12 is preferably provided with a connector 18 (FIG. 3). The connector 18 allows the tube 12 to be quickly, securely and sealingly connected to the bottom opening 100B of the Urostomy bag 100. The connector 18 also preferably allows the tube 12 to be disconnected from the bag 100 without damaging the bag 100. The connector 18 is preferably similar to the ACCUSEAL® adapters sold by ConveTec Limited located in Deeside, United Kingdom. However, any well known method of sealingly attaching the tube 12 to the bottom opening 100B of the bag 100 may be used. Alternatively, the tube 12 of the drainage system 10 could be permanently attached to the bottom opening 100B of the bag 100. Therefore, the bag 100 and the drainage system 10 would be a single unit.

A shut-off clamp 14 is provided at the discharge end 12B of the tube 12 (FIG. 3). The shut-off clamp 14 preferably mounts on the outside of the tube 12 adjacent the discharge end 12B of the tube 12 and closes off the end 12B of the tube 12 by pinching the tube 12 shut. Alternatively, the clamp 14 can be similar to the valve 102 located in the bottom opening 100B of the bag 100 and can be located inside of the end 12B of the tube 12. Any well known clamp or valve for closing a conduit to prevent fluid flow can be used. In the preferred embodiment, the clamp 14 is compact, lightweight and inexpensive as well as easy to use.

Figure 1:
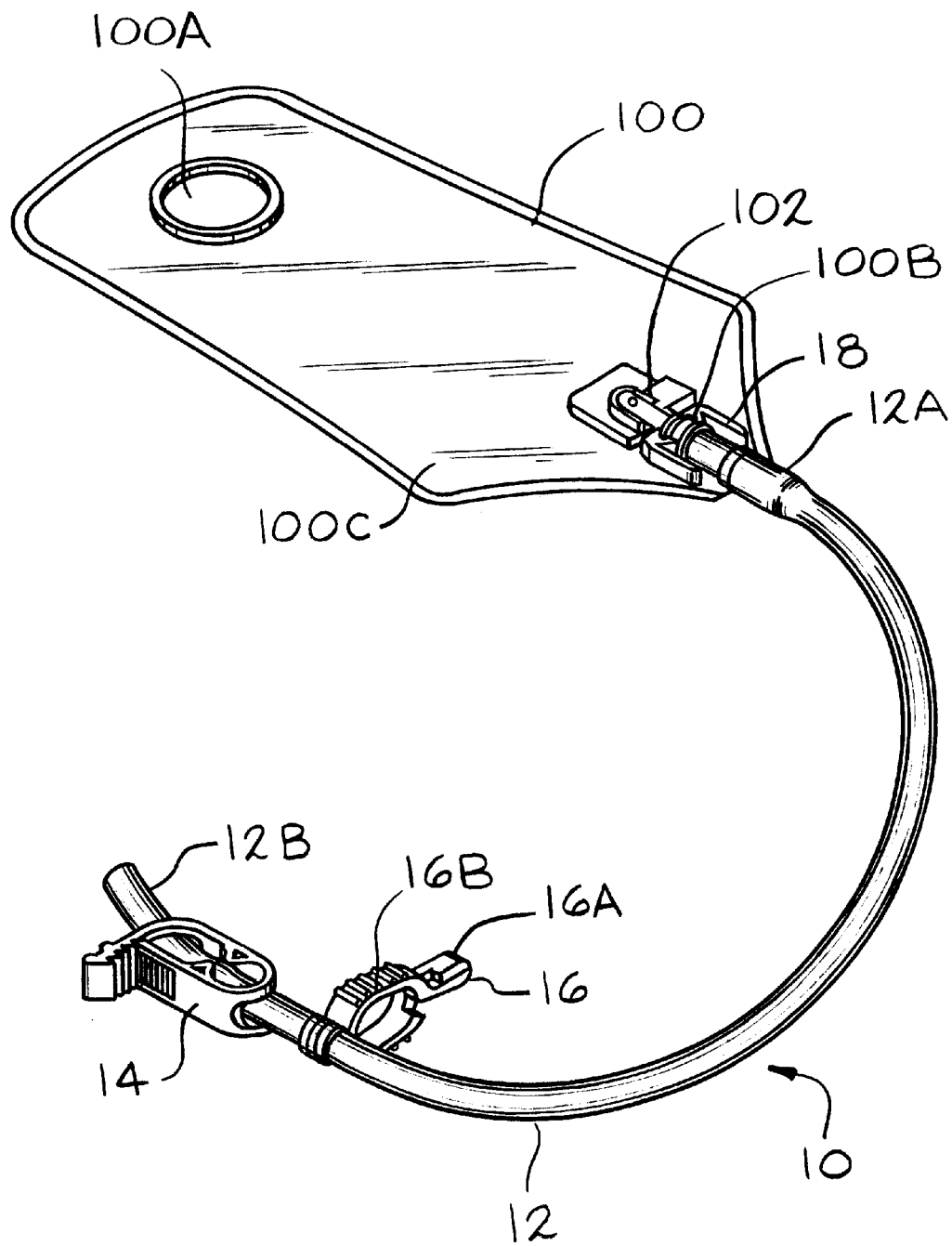
FIG. 1 is a perspective view of a Urostomy bag 100 having the drainage system 10 connected to the bottom opening 100B of the bag 100.

The attachment clip 16 is preferably secured to the tube 12 adjacent the discharge end 12B of the tube 12. As shown in FIG. 1, the clip 16 is preferably secured to the outside of the tube 12 and does not effect the flow of fluid within the tube 12. The clip 16 can be attached to the tube 12 by any well known means which does not effect the flow through the tube 12. The clip 16 can be any well known fastener such as a snap or a hook and loop fastener. In the preferred embodiment, the clip 16 is a squeeze type clip where the jaws 16A of the clip 16 are opened by pressing the sides of the body 16B of the clip 16 together. Preferably, the clip 16 or fastener is inexpensive, lightweight and easy to use. Preferably, the clip 16 does not require alteration of a user's clothing. In an alternate embodiment (not shown), the shut-off clamp 14 and attachment clip 16 are constructed as a single, unitary piece.

The drainage system 10 is for use during the day when a user 150 has to empty the Urostomy bag 100 directly into a waste receptacle. The drainage system 10 is particularly useful when the user 150 has to drain the Urostomy bag 100 in a public restroom. To use the drainage system 10, the user 150 preferably attaches the drainage tube 12 to the bottom opening 100B of the bag 100 prior to mounting the bag 100 on the stoma of the user 150. Alternatively, the drainage tube 12 can be attached to the bag 100 after the bag 100 is positioned on the user 150. The drainage system 10 could also be provided as a unitary piece with the bag 100. Once the bag 100 is in place, the user 150 uses the attachment clip 16 to attach the discharge end 12B of the tube 12 adjacent the inner side of the front opening 154A of his trousers 154 (FIG. 2). In the preferred embodiment, the attachment clip 16 is attached to the undergarments 156 of the user 150 adjacent the front opening 154A of the user's trousers 154. Preferably, the tube 12 can be clipped anywhere on the user's clothing or undergarments 156 where the end of the tube 12 and clip 16 are easily accessible to the user 150 upon the user 150 opening the front opening 154A of his trousers 154. In the preferred embodiment, the clip 16 is attached such that the discharge end 12B of the tube 12 is above the bottom opening 100B of the bag 100 and the opening of the tube 12 is pointing upwards (FIG. 2). This positioning of the discharge end 12B of the tube 12 reduces the risk of fluid leaking from the discharge end 12B of the tube 12 due to a defective clamp 14. Once the drainage system 10 and bag 100 are in position, the user 150 opens the valve 102 at the bottom opening 100B of the bag 100. Opening the valve 102 upon securing the drainage tube 12 allows the user 150 to quickly drain the bag 100 and eliminates the need for the user 150 to adjust his clothing to obtain access to the valve 102 at the bottom of the bag 100 each time the bag 100 is to be drained.

To drain the bag 100, the user 150 preferably positions himself adjacent the opening of a waste receptacle. The user 150 then opens the front opening 154A of his trousers 154 and unclips the attachment clip 16 from his clothing. Alternatively, if the user 150 is wearing clothing not having a front opening 154A, the user 150 would remove the clothing covering the clip 16 or move the clothing such as to gain access to the clip 16. Preferably, the user 150 need only unfasten or remove a minimum of clothing. Once the user 150 has access to the clip 16, the user 150 unattaches the clip 16 from his clothing. The user 150 then positions the discharge end 12B of the drainage tube 12 above and in close proximity to the opening of the waste receptacle. The length of the drainage tube 12 is such that the user 150 can empty the bag 100 into the waste receptacle without excess spillage of waste fluid. In the preferred embodiment, the user 150 is able to drain the bag 100 into the waste receptacle in the standing position without risk of splashing waste fluid on his clothing or the waste receptacle.

Upon opening of the clamp 14, the bag 100 preferably empties fully due to gravity. However, the user 150 may assist in emptying the bag 100 by lightly squeezing the bag 100. Once the bag 100 is empty, the user 150 closes the shut-off clamp 14 at the discharge end 12B of the tube 12. The user 150 then removes any remaining waste fluid from the discharge end 12B of the tube 12. Once the tube 12 is dry, the attachment clip 16 is reattached to the user's undergarments 156 or inner surface of the user's trousers 154. The user 150 then refastens and puts on any clothing that was unfastened or removed to gain access to the clip 16.

In the preferred embodiment, when the drainage system 10 is in use and attached to the Urostomy bag 100, the drainage system 10 is not detectable through the user's clothing. For sanitary reasons, a new drainage system 10 is preferably used each time a user 150 replaces a bag 100.

It is intended that the foregoing description be only illustrative of the present invention and that the present invention be limited only by the hereinafter appended claims.

I claim:

1. An improved Urostomy bag having a top opening for securing to a user and a bottom opening for draining the bag, the bottom opening having a valve means for opening and closing the bottom opening, the improvement which comprises:

(a) a drainage tube having opposed ends and connected at one of the ends on the bottom opening of the bag and having a diameter and size which allows the tube to be folded between the ends so that the second end of the tube is able to be attached adjacent a waist of a user when the tube is full of fluid;

(b) a shut-off means mounted on the other end of the tube for opening and closing the other of the ends of the tube; and (c) an attachment means mounted on the tube between the ends of the tube to allow attachment of the tube to clothing being worn by the user.

2. The bag of claim 1 wherein the drainage tube with the shut-off means and attachment means is removable from the Urostomy bag.

3. The bag of claim 2 wherein one end of the drainage tube has a connector which removably connects the end of the tube to the bottom opening of the bag.

4. The bag of claim 1 wherein the attachment means is configured to attach the tube to an undergarment adjacent a front opening of a user's trousers.

5. The bag of claim 1 wherein the tube has a length such as to extend from the bottom opening of the bag through a front opening in a user's trousers.

6. The bag of claim 1 wherein the shut-off means is a clamp mounted on an outside surface of the drainage tube.

7. The bag of claim 1 wherein the tube is flexible such as to be easily positioned over a waste receptacle.

8. The bag of claim 1 wherein the attachment means is a clip.

9. The bag of claim 1 wherein the attachment means is mounted on the tube adjacent the second end of the tube.

10. The bag of claim 1 wherein the tube is capable of being attached to the user's clothing such that one of the ends of the tube is positioned above the other of the ends of the tube.

11. A method for draining waste fluid from a Urostomy bag which is capable of being secured to a user, which comprises the steps of:

(a) providing a drainage system underneath clothing being worn by the user connected to a bottom opening of the Urostomy bag which includes a tube having first and second ends and configured to be connected at the first end to the bottom opening of the Urostomy bag and having a diameter and size which allows the tube to be folded between the ends so that the second end of the tube is able to be attached adjacent a waist of a user when the tube is full of fluid; a shut-off means mounted on the second end of the tube for opening and closing the second end of the tube; and an attachment means mounted on the tube between the ends of the tube to allow attachment of the tube to clothing being worn by the user wherein the first end of the tube is connected to the bottom opening of the Urostomy bag and wherein the tube is attached to the user's clothing using the attachment means;

(b) unfastening the clothing being worn by the user to allow access to the attachment means adjacent the waist of the user;

(c) unattaching the attachment means and the tube from the clothing of the user;

(d) positioning the second end of the tube over a waste receptacle; and (e) opening the shut-off means and allowing the waste fluid to be drained from the bag into the waste receptacle.

12. The method of claim 11 wherein after the waste fluid is drained from the bag, the shut-off means is closed and the attachment means is reattached to the user's clothing and the user's clothing is refastened.

13. The method of claim 11 wherein a second valve means is provided at the bottom opening of the Urostomy bag and wherein prior to step (c), the second valve means is opened.

\* \* \* \* \*

UNITED STATES PATENT AND TRADEMARK OFFICE
CERTIFICATE OF CORRECTION

PATENT NO. : 6,132,408
DATED : October 17, 2000
INVENTOR(S) : Vivian M. Lutz

It is certified that error appears in the above-identified patent and that said Letters Patent is hereby corrected as shown below:

Column 1,
Line 25, "to Schbttes et al" should be -- to Schlottes et al. --.

Column 5,
Line 10, -- a stoma of -- should be inserted after "securing to" and before "a user".
Line 24, "mounted on the tube between the ends of the tube to allow attachment of the tube to clothing being worn by the user" should be
-- mounted on the tube adjacent the second end of the tube to allow attachment of the second end of the tube to clothing being worn by the user adjacent the waist of the user wherein the attachment means --.
Line 36, "wherein the tube has a length such as to extend" should be -- wherein the tube is adapted to extend --.

Signed and Sealed this

Tenth Day of May, 2005

JON W. DUDAS
*Director of the United States Patent and Trademark Office*